United States Patent [19]

Chiesi et al.

[11] Patent Number: 4,775,676

[45] Date of Patent: Oct. 4, 1988

[54] THIAZOLIDINE DERIVATIVES, PROCESS FOR THEIR PREPARATION AND PHARMACEUTICAL COMPOSITIONS

[75] Inventors: Paolo Chiesi; Vittorino Servadio, both of Parma, Italy

[73] Assignee: Chiesi Farmaceutici S.p.A., Parma, Italy

[21] Appl. No.: 930,502

[22] Filed: Nov. 12, 1986

[30] Foreign Application Priority Data

Nov. 13, 1985 [IT] Italy ............................... 22815 A/85

[51] Int. Cl.⁴ ................. C07D 277/06; A61K 31/425
[52] U.S. Cl. .................................... 514/365; 548/200
[58] Field of Search ......................... 548/200; 514/365

[56] References Cited

U.S. PATENT DOCUMENTS 4,477,458 10/1984 Mora ................................... 548/200
4,499,102 2/1985 Oya ..................................... 548/200

OTHER PUBLICATIONS

Iwase, Anal. Biochem. 78 340, (1977), Abstract Only.

Primary Examiner—Robert Gerstl
Attorney, Agent, or Firm—Bucknam and Archer

[57] ABSTRACT

Compounds of formula I

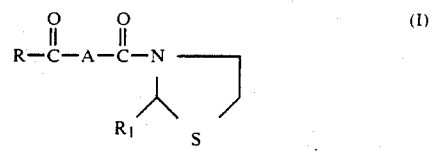

wherein A represents:
a saturated or unsaturated acyclic residue;
a saturated cyclic or heterocyclic residue;
a saturated or unsaturated bicyclic residue; and R represents OH, a $C_1$-$C_4$ alkoxy group or a straight or heterocycle aminoresidue; $R_1$ represents hydrogen, an alkyl group or an aromatic or heteroaromatic residue.

Compounds I are endowed with valuable therapeutic characteristics.

9 Claims, No Drawings

THIAZOLIDINE DERIVATIVES, PROCESS FOR THEIR PREPARATION AND PHARMACEUTICAL COMPOSITIONS

The present invention refers to thiazolidine derivatives, a process for the preparation thereof and pharmaceutical compositions containing them. In particular, the invention refers to the general formula I

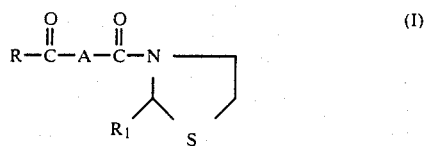

wherein A represents:
- a straight or branched $C_1$–$C_5$ saturated acyclic residue or an unsaturated $C_3$–$C_6$ acyclic residue, optionally interrupted by heteroatoms, such as S, O or N and optionally substituted by alkyl, amino, alkoxy or carbonyl groups;
- a saturated cyclic or heterocyclic residue or an unsaturated $C_3$–$C_6$ monocyclic residue optionally substituted by alkyl, amino or alkoxy groups;
- a saturated bicyclic residue having $C_3$–$C_4$ to $C_6$–$C_6$ ring systems, such as bicyclo-[2,2,1]-hepta-1,2-diyl or bicyclo-[2,2,2]-octa-1,2-diyl,
- an unsaturated bicyclic residue having $C_3$–$C_4$ to $C_6$–$C_6$ ring systems, such as bicyclo-[2,2,1]-hepta-5-ene-1,2-diyl or bicyclo-[2,2,2]-octa-1,2-diyl, optionally containing one or more heteroatoms, such as S or O, and optionally substituted by alkyl substituent groups;

R represents OH, straight or branched $C_1$–$C_4$ alkoxyl, an amino group having formula $NR_2R_3$ wherein $R_2$ and $R_3$, which are the same or different, represent H, a carboxylalkyl group or $R_2$ and $R_3$, taken together with the nitrogen atom, form a 5- or 6-membered heterocyclic residue, optionally containing other heteroatoms such as thiazolidin-3-yl;

$R_1$ represents H, a straight or branched $C_1$–$C_4$ alkyl or a saturated or unsaturated cyclic residue.

When A represents a saturated $C_1$–$C_5$ acyclic residue, it is preferably methylene, ethylene, propylene, 2-methyl-propylene whereas when A represents an unsaturated $C_3$–$C_6$ acyclic residue, it is preferably 1-propene-1,3-diyl, 2-butene-1,4-diyl or 1,6-hexadienyl.

Particularly preferred compounds are those in which A represents 1,2-cyclohexyl, 1,2- or 1,3-cyclopentyl groups substituted by $C_1$–$C_4$ alkyl groups; bicyclo[2,2,1]-hepta-5-ene-1,2-diyl; a lower alkylene such as ethylene; or a straight or branched saturated acyclic residue interrupted by a sulphur atom such as 2-(1-amino)ethylthiomethyl or 1-ethylthiomethyl.

When R is OH, compounds I may be salified with pharmaceutically acceptable organic or inorganic bases, said salts being also an object of the present invention. Compounds of formula (I) may be in racemic, diastereoisomeric or optically active form, all these forms falling within the scope of the present invention.

The novel thiazolidine derivatives object of the present invention show such valuable pharmacological characteristics, as to be used in therapy as mucosecretolytic, antiinflammatory or hepatoprotecting agents.

The process for the preparation of thiazolidine derivatives of general formula (I) consists in reacting thiazolidine base, or substituted derivatives thereof, with an equivalent amount of a mono or dicarboxylic derivative, preferably a mono- or dihalide or with a cyclic anyhydride in an appropriate solvent.

Salified thiazolidine, generally as an hydrochloride, may be used, adding in this case an equivalent amount of an organic or inorganic base in order to release the thiazolidine or an analogue thereof in the reaction medium.

As solvents, aprotic solvents such as chloroform, methylene chloride, benzene, dimethylformamide, etc. may by used.

The reaction may be carried out at temperatures ranging from 0° C. to the solvent's reflux temperature, for a time from 1 to 10 hours, depending on the nature of the reagents and solvents.

For the preparation of thiazolidine derivatives of general formula I, wherein A represents a straight chain interrupted by a sulfur atom, thiazolidine haloalkyl derivatives (obtained by the above described process) are further reacted with mercapto derivatives, such as L-cysteine, mercaptopropionylglycine or mercaptopropionic acid in a polar solvent.

An amount of organic or inorganic base is added to the reaction medium so as to neutralize the acid developing during the reaction course. The used solvents are preferably polar solvents, such as water, ethanol, dimethylformamide.

The reaction may be carried out at temperatures ranging from 0° C. to the solvent's reflux temperature, for a time from 1 to 24 hours, depending on the nature of the reagents and of the solvents.

The salts object of the invention may be obtained by addition of equivalent amounts of inorganic bases, such as alkali or alkali-earth metal hydroxides or carbonates, or organic bases, preferably aminoacids, such as lysine or arginine, in a polar medium.

Esters of the acids of general formula I may be prepared by one of the known esterification method, preferably by reaction of the acid with an excess of alcohol in a polar aprotic medium in the presence of a mineral acid as a catalyst.

The invention will be illustrated in further detail by means of the following non-limiting Examples.

EXAMPLE 1

3-[3-[(2-Ethyl)-thiazolidine]carbonyl]-bicyclo-[2,2,1]-hepta-5-ene-2-carboxylic acid (2)

35 G (228 mM) of 2-ethylthiazolidine HCL, 19.72 g (234 mM) of sodium bicarbonate and 0.5 ml of $H_2O$ were added to a solution containing 36.31 g (221 mM) of nadic anhydride in 350 ml of chloroform. The mixture was stirred at room temperature for 24 hours, filtered and evaporated. The obtained yellow oil was dissolved in 50 ml of acetone and 400 ml of acetone were added, under stirring. The solution was left to stand overnight, and the white crystalline solid was filtered and washed with ethyl ether.

35.95 G (57.8% yield) of product (2) were so obtained. M.p.=131°–134° C.

Elemental analysis: (for $C_{14}H_{19}NO_3S$; MW=281.37). Calc. %: C, 59.76; H, 6.81; N, 4.98. Found %: C, 59.85; H, 6.89; N, 5.04.

IR and NMR spectra in agreement.

By the same process, 20 g (159 mM) of thiazolidine hydrochloride, 26.12 g (159 mM) of nadic anhydride and 13.39 g (159 mM) of NaCHO$_3$ were reacted in 103 ml of CH$_2$Cl$_2$ and 2.4 ml of H$_2$O.

A white solid, melting at 146°–147° C., consisting of 3-[(3-thiazolidyl)-carbonyl]-bicyclo-[2,2,1]-hepta-5-ene-2-carboxylic acid (3), was obtained.

Elemental analysis: (for C$_{12}$H$_{15}$NO$_3$S; MW=253). Calc. %: C, 56.97; H, 5.98; N, 5.54. Found %: C, 56.60; H, 5.67; N, 5.27.

IR and NMR spectra in agreement.

In similar conditions, 20 g (159 mM) of thiazolidine hydrochloride, 15.47 g (155 mM) of succinic anhydride were reacted in 103 ml of CH$_2$Cl$_2$ adding slowing 13.39 g (159 mM) of NaHCO$_3$. A compound melting at 72°–75° C., consisting of 4-oxo-4-(3-thiazolidyl)-butanoic acid (4) was obtained.

(C$_7$H$_{11}$NO$_3$S, MW=189.24). IR and NMR spectra in agreement.

EXAMPLE 2

A solution of 24 g (0.27 ml) of thiazolidine in 200 ml of CH$_2$Cl$_2$ was slowly added, under stirring, to a solution containing 40.16 g (0.24 ml) of anhydride of 4-methyl-1,2-dicyclohexanedicarboxylic acid in 100 ml of CH$_2$Cl$_2$.

The mixture was stirred for 12 hours at room temperature and then the excess thiazolidine was extracted with a 1M solution of HCl ($\approx$ 50 ml). The organic solution was evaporated, the solid obtained was dissolved with 30 ml of warm EtOH and, after cooling, 300 ml of water were added. A white solid was obtained by precipitation, which was filtered, washed with water and dried in oven under vacuum at 50° C.

The solid, melting at 138°–146° C., comprises the following structural isomers:
 4-methyl-2-[(3-thiazolidyl)-carbonyl]-cyclohexanecarboxylic acid (5a);
 5-methyl-2-[(3-thiazolidyl)-carbonyl]-cyclohexanecarboxylic acid (5b);
which were separated by means of the commonly used techniques, namely by chromatography.

By the same process, reacting camphoric anhydride and thiazolidine base, a compound melting at 149°–178° C. was obtained.

Elemental analysis: for C$_{13}$H$_{21}$NO$_3$S, MW=271.383. Calc. %: C, 57.54; H, 7.80; N, 5.16. Found %: C, 57.35; H, 7.81; N, 5.18.

The product obtained comprised the following structural isomers:
 3-[(3-thiazolidyl)-carbonyl]-2,2,3-trimethyl-cyclopentane-carboxylic acid (6a);
 3-[(3-thiazolidyl)-carbonyl]-1,2,2-trimethyl-cyclopentane-carboxylic acid (6b);
which were separated by means of the commonly used techniques, namely by chromatography.

EXAMPLE 3

1,4-Bis-(3-thiazolidyl)-1,4-dioxo-butane (7)

A solution of 17.36 g (112 mM) of succinyl dichloride was slowly added to a solution of 21.02 g (236 mM) of thiazolidine, 24 g (237 mM) of triethylamine in 250 ml of dichloroethane, under stirring and in an ice-bath. The mixture was stirred for 1 hour at low temperature (ice-bath) and then at room temperature for 1 hour. The solution was then filtered and evaporated. The solid was taken up with chloroform ($\approx$ 300 ml) and washed with water.

The organic phase was dried on sodium sulfate and evaporated.

19.1 G of white solid (yield 65.5%). melting at 109°–114° C. (C$_{10}$H$_{16}$N$_2$O$_2$S$_2$, MW=260.37), were obtained. IR and NMR spectra in agreement.

EXAMPLE 4

2-Amino-3-[[(3-thiazolidyl)-carbonylmethyl]thio]propionic acid (8)

A solution of sodium hydroxide 5N was added to a 500 ml flask containing 36.35 g (0.3 M) of L-cysteine in 120 ml of water, cooling to +5° C. by means of an ice-bath, till pH=8. 49.7 G (0.3 M) of 3-(chloroacetyl)-thiazolidine were slowly added to the obtained solution. keeping the temperature at 5° C. The mixture was left under stirring for 2 hours, keeping the reaction mixture at pH 7–7.5 by addition of NaOH 5N.

The mixture was acidified with 10% hydrochloric acid up to pH=4 and left under stirring for 4 hours. The solvent was then partially evaporated, filtered and the obtained solution was evaporated. The residue was taken up with 400 ml of methanol, filtered and evaporated again.

8.33 G of a solid, which was purified by column chromatography (silica gel 6D), eluent n-propanol/ammonia=70/30. M.p.=173°–178° C. (dec.), were obtained.

Elemental analysis: (for C$_8$H$_{14}$N$_2$O$_3$S$_2$; MW=250.33). Calc. %: C, 38.38; H, 5.64; N, 11.19. Found %: C, 38.13; H, 5.59; N, 11.10.

IR and NMR spectra in agreement.

According to a similar process, equimolar amounts (289 mM) of N-(2-mercapto-propionyl)-glycine and of 3-(chloroacetyl)-thiazolidine, were reacted, yielding 43.8 g (52% yield) of 2-[2-[(3-thiazolidyl)carbonylmethylthio]-propionamide]acetic acid (9) (m.p.=122°–126° C.).

Elemental analysis: (for C$_{10}$H$_{16}$N$_2$O$_4$S$_2$; MW=292.37). Calc. %: C, 41.08; H, 5.51; N, 9.58. Found %: C, 41.00; H, 5.25; N, 9.33.

IR and NMR spectra in agreement.

The acids 2–9 may be transformed into the corresponding salts by addition of an organic or inorganic base.

By way of an example, the following compounds have been prepared:
4-oxo-4-(3-thiazolidyl)butanoic acid sodium salt (10)

Elemental analysis: (for C$_7$H$_{10}$NO$_3$SNa; MW=211.22). Calc. %: C, 39.81; H, 4.77; N, 6.63. Found %: C, 39.60; H, 4.52; N, 6.42;
 4-methyl-2-[(3-thiazolidyl)carbonyl]-cyclohexanecarboxylic acid lysine salt (11)

Elemental analysis: (for C$_{19}$H$_{33}$N$_3$O$_5$S; MW=403.55). Calc. %: C, 53.57; H, 8.24; N, 10.41. Found %: C, 53.28; H, 8.40; N, 10.50;
 -3-[(3-thiazolidyl)-carbonyl]-2,2,3-trimethyl-cyclopentanecarboxylic acid lysine salt (12)

Elemental analysis: (for C$_{19}$H$_{35}$N$_3$O$_5$S; MW=417.57). Calc. %: C, 54.65; H, 8.45; N, 10.06; S, 7.63. Found %: C, 54.40; H, 8.75; N, 10.08; S, 7.36.

Compounds of general formula (I) according to the present invention, show valuable pharamacological characteristics, particularly antiinflammatory and mucosecretolytic activities, therefore, compounds (I) may be advantageously used in humans, for the treatment of respiratory apparatus diseases, such as bronchitis, tracheobronchitis, pharyngitis, rhinopharyngitis, etc.

The pharmacological tests have been carried out using as reference compounds similar well-known substances, commonly used in therapy for the treatment of the above pathological conditions.

Toxicity after single administration

IVA:NMRI (SPF) mice, fasted for 18 hours before treatment with water ad libitum, were used. The compounds, dissolved or suspended in a 0.2% Tween ® 80 aqueous solution, were administered orally, at constant concentration (10%). According to the death-rate observed after 7 days from treatment, the approximate $LD_{50}$ values, reported in Table 1, were interpolated on Probi ts chart.

Mucosecretodynamic activity

Male IVA-NMRI (SPF) mice, housed for at least 1 week under standard conditions, fasted (water ad libitum) for 18 hours before treatment, were used.

The used method, relying on the ability of fluorescein to be excreted even in the respiratory tract, is according to Mawatari H. (Kagoshima Daigaku Igaku Zasshi 27, 561, 1976) and to Graziani G. and Cazzulani P. (Farmaco (Pra) 36, 167, 1981).

The compounds, dissolved or suspended in 20 ml/kg of a 0.2% Tween ® 80 aqueous suspension, were administred orally 90 minutes before the intravenous injection of 1% (5 ml/kg) fluorescein. Animals treated p.o. with the only vehicle were used as a control group. After 30 minutes from the fluorescein injection the animals were killed and subjected to incannulation of the trachea. Then the respiratory tract was washed and the spectrophotometric dosage of the fluorescein was carried out against phosphate buffer on the so collected eluate, suitably diluted with phosphate buffer and centrifugated.

The amount of fluorescein was determined by means of a calibration curve prepared under the same experimental conditions and the excretion was expressed as ng/hour/10 g body weight. For each experimental session the percent increases of excretion versus controls were calculated. According to said values the regression log dose-effect straight-lines were determined and the $ED_{50}$ values, reported in Table 1, were interpolated.

"In vitro" mucolytic activity 0.2 Ml of a 10% DMSO solution of the compounds under test were homogeneously added to 1.8 ml of a 6% aqueous solution of porcine gastric mucine (Knock-Light 4065-00, batch 81063). Control samples were similarly added with the vehicle only. After incubation at 25° C. for 30 minutes, the analysis of the rheologic characteristics was carried out by means of Contraves Low-Shear 30 sinus viscosimeter provided with an oscillating device for the study of the viscoelasticity. The dynamic measurements of the viscoelasticity were carried out at a single frequency (0.075 Hz), using an appropriate concentrical cylinder measurement system, particularly suited for bronchial mucus (Contraves MS-LS 1-1).

The rheogramm was recorded on X/Y Rikadenki 11T recorder and the viscosity (G') and elastic modulus ($\eta$) determination was carried out by means of vectorial calculation.

The percent decreases versus control samples, reported in Table 1, were determined from the means of the values of said parameters (at least 7 replications per sample).

TABLE

| Compounds | Acute toxicity $LD_{50}$ approx. mg/kg p.o. | Mucosecretodynamic-mucolytic activity | | |
|---|---|---|---|---|
| | | "in vivo" fluorescein test $ED_{50}$ mg/kg p.o. | "in vitro" % decrease | |
| | | | elasticity (G') | viscosity ($\eta$) |
| 2(CHF 1208) | ≃3000 | N.D. | 33 | 58 |
| 3(CHF 1169) | ≃1500 | 170 | 28 | 41 |
| 4(CHF 1159) | ≃4000 | N.D. | 24 | 49 |
| 5(CHF 1196) | ≃3000 | 200 | 27 | 54 |
| 6(CHF 1195) | >4000 | 230 | 21 | 34 |
| 7(CHF 1193) | ≃3000 | ≃750 | 22 | 41 |
| 8(CHF 1261) | >4000 | N.D. | 4 | 3 |
| 9(CHF 1230) | >4000 | N.D. | 21 | 40 |
| 10(CHF 1211) | >4000 | N.D. | 10 | 11 |
| 11(CHF 1224) | >4000 | 300 | 6 | 9 |
| 12(CHF 1223) | >4000 | 310 | 13 | 0 |
| S—carboxy-methyl-cysteine | >4000 | 1900 | N.D. | N.D. |
| N—acetyl-L-cysteine | 4400 | 1300 | 39 | 53 |

N.D. = Not determined.

The compounds under test possess a remarkable mucosecretodynamic-mucolytic activity, particularly in the fluorescein "in vivo" test, whereas similar reference compounds exhibit a relatively poor activity.

The present invention refers moreover to pharmaceutical compositions containing as the active principle a compound of formula (I), as defined above, as such or in form of a pharmaceutically acceptable salt thereof, in combination with at least one pharmaceutically acceptable excipient.

The compositions may be administered by the oral, rectal, parenteral route or by inhalation, respectively, in form of capsules, tablets, granules, suspensions syrups or the like, suppositories, solutions, suspensions or powders respectively for the parenteral or inhalatory route.

For the preparation of pharmaceutical compositions for the oral administration in unitary dose, the active principle may be mixed with a solid, powdered excipient such as lactose, saccharose, sorbitol, mannitol, potato, cereal or maize starch or amylopectine, a cellulose derivative or gelatine, and it can comprise also lubricants such as talc, magnesium or calcium stearate, polyethylenglycol or silica. The tablets can be variously coated according to well known methods in the pharmaceutical practice. Hard gelatine capsules may comprise granules of the active principle together with a solid, powdered excipient such as lactose, saccharose, sorbitol, mannitol, starches of the above cited kind, cellulose derivatives or gelatine, and they may comprise also stearic acid or magnesium stearate or talc.

Granules in sachets may be prepared from cellulose derivatives, precipitated silica, flavours and sugars or polyalcohols such as saccharose, mannitol, sorbitol etc.

For the preparation of suspensions for oral use, the active principles may be dissolved in aqueous solutions of sugars or polyalcohols with the addition of preservatives and flavouring agents.

Unitary doses for the rectal administration may be in form of suppositories containing the active principle in combination with a neutral fatty base (i.e. fatty acid glycerides) or with hydrosoluble or self-emulsifying excipients (i.e. polyethylenglycol mixtures).

For injectable formulations for parenteral administrations, the excipients may be a sterile, pharmaceutically acceptable liquid such as water or a polyvinylpyrrolidone aqueous solution or again an oil such as peanut oil and optionally a stabilizing and/or buffering agent.

The unitary dose for the formulations for oral use such as tablets, capsules, granules and for rectal, parenteral or inhalatory formuations may range from 10 to 500 mg of active principle. The concentration of the active principle in the suspensions for oral use may range from 0.1 to 5%.

The following formulations are reported by way of example.

| | | Composition with two different dosages | |
|---|---|---:|---:|
| Formulation in capsules | | | |
| Compound (3) | mg | 100 | 200 |
| Starch | mg | 20 | 30 |
| Lactose | mg | 172 | 57 |
| Polyvinylpyrrolidone | mg | 5 | 10 |
| Magnesium stearate | mg | 3 | 3 |
| Formulation in sachets | | | |
| Compound (3) | mg | 100 | 200 |
| Hydroxypropylmethylcellulose | mg | 25 | 50 |
| Precipitated silica | mg | 2 | 4 |
| Citrus fruit flavour | q.s. | | q.s. |
| Sorbitol | q.s. to g 5 | | 5 |
| Suspension for oral use | | | |
| Compound (5) | mg | 1000 | |
| Carboxymethylcellulose | mg | 80 | |
| Microcrystalline cellulose | mg | 920 | |
| Sorbitol | g | 10 | |
| Methyl p-hydroxybenzoate | mg | 135 | |
| Propyl p-hydroxybenzoate | mg | 15 | |
| Citrus fruit flavour | q.s. | | |
| Purified water | q.s. to ml | 100 | |
| Formulation in suppositories | | | |
| (a) Compound (3) | mg | 100 | 200 |
| Solid semi-synthetic glycerides | q.s. to mg | 2000 | 2000 |
| (b) Compound (5) | mg | 100 | 200 |
| Butylhydroxyanisole | mg | 2 | 2 |
| Polyoxyethylenglycols | q.s. to mg | 2000 | 2000 |
| Formulation in vial for aerosol and injectable use | | | |
| Compound (11) | mg | 100 | 400 |
| Dibasic sodium phosphate | mg | 0.3 | 0.3 |
| Monobasic sodium phosphate | mg | 5.5 | 5.5 |
| Sodium chloride | mg | 0.7 | — |
| Water for injection | q.s. to ml | 2 | 2. |

We claim:
1. A compound of formula I

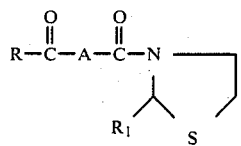

wherein A is:
(1) straight or branched $C_1$–$C_5$ saturated hydrocarbon radical which is unsubstituted or substituted by $C_1$–$C_4$ alkyl, amino, or $C_1$–$C_4$ alkoxy;
(2) straight or branched $C_1$–$C_5$ saturated hydrocarbon radical wherein the carbon atoms of said radical are interrupted by S, O or N, said radical being unsubstituted or substituted by $C_1$–$C_4$ alkyl, amino or $C_1$–$C_4$ alkoxy;

(3) a cycloaliphatic 5- or 6- member ring which is unsubstituted or substituted by $C_1$–$C_4$ alkyl, amino or $C_1$–$C_4$ alkoxy;
(4) an unsaturated bicyclic radical having $C_3$–$C_4$ to $C_6$–$C_6$ rings;
R is OH, $C_1$–$C_4$ alkoxy, an amino group of formula $NR_2R_3$ wherein $R_2$ and $R_3$ are the same or different and each is H, a carboxyalkyl group or $R_2$ and $R_3$ together with the nitrogen atom to which they are attached form a thiazolidinyl ring;
$R_1$ is H, $C_{1-4}$ alkyl;
and when R is OH, addition salts thereof with a pharmaceutically acceptable organic or inorganic base.

2. A compound according to claim 1 wherein A is ethylene, 2-(1-amino)-ethylthiomethyl or 1-ethylthiomethyl.

3. A compound according to claim 1 wherein A is 4-methyl-1,2-cyclohexyl or 1,2,2-trimethyl cyclopentyl.

4. A compound according to claim 1, selected from the group consisting of:
3-[3-[(2-ethyl)thiazolidyl]carbonyl]bicyclo-[2,2,1]-hepta-5-ene-2-carboxylic acid;
4-oxo-3-(3-thiazolidyl)butanoic acid and corresponding sodium salt;
4-methyl-2-[(3-thiazolidyl)carbonyl]cyclohexanecarboxylic acid and corresponding lysine salt;
5-methyl-2-[(3-thiazolidyl)carbonyl]cyclohexanecarboxylic acid and corresponding lysine salt;
3-[(3-thiazolidyl)carbonyl]-2,2,3-trimethyl-cyclopentane carboxylic acid and corresponding lysine salt;
3-[(3-thiazolidyl)carbonyl]-1,2,2-trimethyl-cyclopentane carboxylic acid and corresponding lysine salt;
1,4-bis-(3-thiazolidyl)-1,4-dioxo-butane;
2-amino-3-[[(3-thiazolidyl)carbonylmethyl]thio]propionic acid;
2-[2-[(3-thiazolidyl)carbonylmethyl]propionamide]-acetic acid.

5. A compound according to claim 1 wherein A is bicyclo-[2,2,1]-hepta-5-ene-1,2-diyl or bicyclo[2,2,2]-octa-1,2-diyl.

6. A compound according to claim 1 wherein said R is the group

and is the thiazolidin-3-yl.

7. A pharmaceutical composition having mucosecretolytic, antiinflammatory and hepatoprotecting activity containing as the active principle a compound of formula (I) according to claim 1 or a pharmaceutically acceptable salt thereof and at least one pharmaceutically acceptable carrier.

8. A composition according to claim 7 in form of capsules, tablets, granules, suppositories or vials, containing from 10 to 500 mg of said active principle per unit dose.

9. A composition according to claim 7 in the form of a suspension for oral use wherein the concentration of said active principle is 0.1–5%.

* * * * *